(12) United States Patent
Gauvreau

(10) Patent No.: US 10,941,154 B2
(45) Date of Patent: Mar. 9, 2021

(54) HYDROGENATION PROCESS FOR PREPARING OXYCODONE HYDROCHLORIDE FROM 14-HYDROXYCODEINONE

(71) Applicant: Johnson Matthey Public Limited Company, London (GB)

(72) Inventor: Paul Gauvreau, Paulsboro, NJ (US)

(73) Assignee: Johnson Matthey Public Limited Company, London (GB)

( * ) Notice: Subject to any disclaimer, the term of this patent is extended or adjusted under 35 U.S.C. 154(b) by 0 days.

(21) Appl. No.: 16/622,352

(22) PCT Filed: Jun. 12, 2018

(86) PCT No.: PCT/GB2018/051595
§ 371 (c)(1),
(2) Date: Dec. 13, 2019

(87) PCT Pub. No.: WO2018/234748
PCT Pub. Date: Dec. 27, 2018

(65) Prior Publication Data
US 2020/0199137 A1 Jun. 25, 2020

Related U.S. Application Data

(60) Provisional application No. 62/522,392, filed on Jun. 20, 2017.

(51) Int. Cl.
*C07D 491/08* (2006.01)

(52) U.S. Cl.
CPC .................. *C07D 491/08* (2013.01)

(58) Field of Classification Search
None
See application file for complete search history.

(56) References Cited

U.S. PATENT DOCUMENTS

| | | | |
|---|---|---|---|
| 7,129,248 B2 | 10/2006 | Chapman et al. | |
| 7,674,799 B2 | 3/2010 | Chapman et al. | |
| 7,674,800 B2 | 3/2010 | Chapman et al. | |
| 7,683,072 B2 | 3/2010 | Chapman et al. | |
| 8,822,687 B2 | 9/2014 | Chapman et al. | |
| 8,916,707 B2 * | 12/2014 | Archer | C07D 489/08 546/45 |
| 9,073,933 B2 | 7/2015 | Chapman et al. | |
| 9,908,891 B2 | 3/2018 | Archer et al. | |
| 9,932,348 B2 | 4/2018 | Giguere et al. | |
| 10,202,396 B2 | 2/2019 | Gebbie et al. | |
| 10,227,354 B2 | 3/2019 | Itov et al. | |
| 10,259,819 B2 | 4/2019 | Chapman et al. | |
| 10,407,434 B2 | 9/2019 | Chapman et al. | |
| 10,428,079 B2 | 10/2019 | Giguere et al. | |
| 10,649,669 B2 | 5/2020 | Matharu et al. | |
| 10,689,389 B2 | 6/2020 | Chapman et al. | |
| 10,696,684 B2 | 6/2020 | Chapman et al. | |
| 2006/0111383 A1 | 5/2006 | Casner et al. | |
| 2008/0132703 A1 | 6/2008 | Cox et al. | |
| 2015/0265598 A1 | 9/2015 | Chapman et al. | |
| 2019/0308986 A1 | 10/2019 | Gebbie et al. | |
| 2020/0199134 A1 | 6/2020 | Giguere et al. | |

FOREIGN PATENT DOCUMENTS

| | | |
|---|---|---|
| EP | 2377866 A1 | 10/2011 |
| WO | 2005097801 A1 | 10/2005 |
| WO | 2014022733 A1 | 2/2014 |

* cited by examiner

*Primary Examiner* — Zinna Northington Davis

(57) ABSTRACT

A process for preparing oxycodone hydrochloride, said process comprising hydrogenating 14-hydroxycodeinone in an alcoholic solvent and hydrochloric acid to form oxycodone hydrochloride, wherein (a) the hydrogenation is carried out in the presence of a heterogeneous platinum group metal (PGM) catalyst and hydrogen gas, (b) the hydrogenation is carried out at one or more temperatures greater than ambient temperature in the presence of a hydrogenation catalyst and hydrogen gas, wherein the solution of 14-hydroxycodeinone and hydrochloric acid is heated to temperature before it is exposed to the hydrogen gas, (c) the oxycodone hydrochloride comprises 6a-oxycodol in an amount <about 0.300 area % as determined by HPLC, characterized in that (d) the pH of the solution of 14-hydroxycodeinone and hydrochloric acid is in the range of about ≥2.5 to about ≤4.5; (e) the process is carried out in one pot, and (f) the oxycodone hydrochloride precipitates out of the solution.

15 Claims, 4 Drawing Sheets

HYDROGENATION PROCESS FOR PREPARING OXYCODONE HYDROCHLORIDE FROM 14-HYDROXYCODEINONE

CROSS-REFERENCE TO RELATED APPLICATIONS

This application is the National Stage of International Application No. PCT/GB2018/051595, filed on Jun. 12, 2018, which claims priority to U.S. Provisional Patent Application Ser. No. 62/522,392, filed on Jun. 20, 2017.

The present invention concerns an improved process for preparing oxycodone hydrochloride having an improved impurity profile.

WO2005/097801 (to Euro-Celtique S.A.) describes processes for the preparation of oxycodone hydrochloride having less than 25 ppm of 14-hydroxycodeinone. The processes involve either:
(a) oxidising the baine to form 14-hydroxycodeinone at a "suitable pH to minimize or eliminate" the production of 8,14-dihydroxy-7,8-dihydroxycodeinone in the 14-hydroxycodeinone. This process is not exemplified.
or
(b) treating previously prepared and isolated oxycodone alkaloid or hydrochloride salt such that oxycodone hydrochloride having less than 25 ppm of 14-hydroxycodeinone is obtained. An exemplified method involves re-hydrogenating the previously prepared and isolated oxycodone alkaloid or hydrochloride salt.

WO2005/097801, however, does not describe a method for preparing oxycodone hydrochloride having less than 25 ppm of 14-hydroxycodeinone from conventionally prepared 14-hydroxycodeinone in a single step. Furthermore, WO2005/097801 is silent regarding the amounts of 6α-oxycodol produced according to the claimed processes.

WO2014/022733 (to Johnson Matthey PLC) describes a process for preparing an oxycodone acid adduct, said process comprising hydrogenating a solution of 14-hydroxycodeinone and an acid to form a solution of the oxycodone acid adduct, wherein the hydrogenation is carried out at one or more temperatures greater than ambient temperature in the presence of a hydrogenation catalyst and hydrogen gas, wherein the solution of 14-hydroxycodeinone and acid is heated to temperature before it is exposed to the hydrogen gas, and wherein the solution of oxycodone acid adduct comprises 6α-oxycodol in an amount ≤0.800 area % as determined by HPLC.

However, WO2014/022733 does not describe a one pot process for preparing oxycodone hydrochloride, wherein the pH is in the range of about ≥2.5 to about ≤4.5 Nor does WO2014/022733 describe a process wherein oxycodone hydrochloride precipitates out of the reaction mixture when the process is carried out in the range of about of ≥ about 30° C. to about ≤60° C.

SUMMARY OF THE INVENTION

We have developed an improved process which overcomes the disadvantages associated with prior art methods. In the one pot process of the present invention, oxycodone hydrochloride with reduced level of 6α-oxycodol precipitates out of the alcoholic solution, therefore lessening and in certain embodiments bypassing the need for further purification. The present process is suitable for the large-scale or industrial manufacture of oxycodone hydrochloride.

In one aspect, therefore, the invention provides a process for preparing oxycodone hydrochloride, said process comprising hydrogenating 14-hydroxycodeinone in an alcoholic solvent and hydrochloric acid to form oxycodone hydrochloride, wherein
(a) the hydrogenation is carried out in the presence of a heterogeneous platinum group metal (PGM) catalyst and hydrogen gas,
(b) the hydrogenation is carried out at one or more temperatures greater than ambient temperature in the presence of a hydrogenation catalyst and hydrogen gas, wherein the 14-hydroxycodeinone in an alcoholic solvent and hydrochloric acid is heated to temperature before it is exposed to the hydrogen gas,
(c) the oxycodone hydrochloride comprises 6α-oxycodol in an amount <about 0.300 area % as determined by HPLC,
characterized in that
(d) the pH of the solution of 14-hydroxycodeinone and hydrochloric acid is in the range of about ≥2.5 to about ≤4.5;
(e) the process is carried out in one pot.

DETAILED DESCRIPTION

Figure 1:
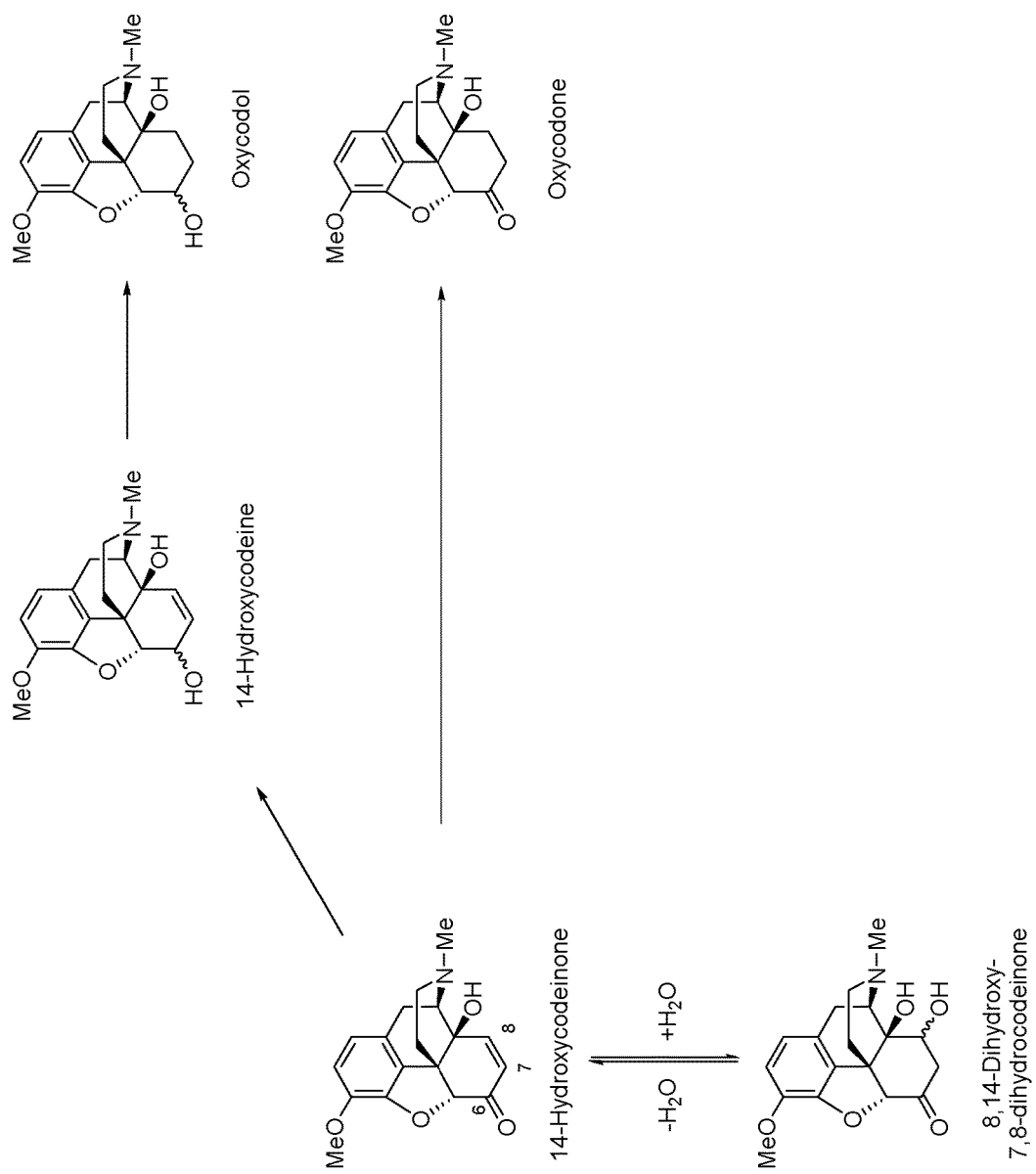
FIG. 1 illustrates the synthetic route of oxycodone.

As mentioned above, in one aspect, the invention provides a process for preparing oxycodone hydrochloride, said process comprising hydrogenating 14-hydroxycodeinone in an alcoholic solvent and hydrochloric acid to form oxycodone hydrochloride, wherein
(a) the hydrogenation is carried out in the presence of a heterogeneous platinum group metal (PGM) catalyst and hydrogen gas,
(b) the hydrogenation is carried out at one or more temperatures greater than ambient temperature in the presence of a hydrogenation catalyst and hydrogen gas, wherein the 14-hydroxycodeinone in an alcoholic solvent and hydrochloric acid is heated to temperature before it is exposed to the hydrogen gas,
(c) the oxycodone hydrochloride comprises 6α-oxycodol in an amount <about 0.300 area % as determined by HPLC,
characterized in that
(d) the pH of the solution of 14-hydroxycodeinone and hydrochloric acid is in the range of about ≥2.5 to about ≤4.5;
(e) the process is carried out in one pot.

The present invention avoids the need to isolate and purify oxycodone base, which is the product of the conventional synthesis. Also, in carrying out the invention in the pH range of about ≥2.5 to about ≤4.5, oxycodone hydrochloride comprising 6α-oxycodol in an amount <about 0.300 area % as determined by HPLC is prepared.

The process comprises hydrogenating 14-hydroxycodeinone in an alcoholic solvent and hydrochloric acid. The alcoholic solvent may be a straight-chain or branched $C_{1-5}$-alkanol and may be selected from the group consisting of methanol, ethanol, propanols (n- or i-), butanols (n-, i- or t-) and pentanols. In one embodiment, the alcoholic solvent may be selected from the group consisting of methanol, ethanol, isopropanol, n-propanol, or mixtures thereof. In one embodiment, the alcoholic solvent is ethanol. In another embodiment, the alcoholic solvent is SDA-3A, which is 96% ethanol denatured with 4% methanol.

The 14-hydroxycodeinone is substantially dissolved in the alcoholic solvent and hydrochloric acid. The dissolution of 14-hydroxycodeinone may be encouraged through the use of an aid such as stirring and/or sonication. The product, oxycodone hydrochloride, is not soluble, and substantially precipitates out of the solution when the temperature of the post-hydrogenation reaction mixture is ≤ about 45° C. However, when the temperature of the post-hydrogenation reaction mixture is ≥ about 45° C., oxycodone hydrochloride is substantially dissolved. When the process is carried out in the range of ≥ about 30° C. to about ≤ about 45° C., the post-hydrogenation reaction mixture can be heated to ≥ about 45° C. after the hydrogen is removed, in order to substantially dissolve the oxycodone hydrochloride. Further filtration (eg. over Celite™) to remove the catalyst and optionally purification may be carried out.

The catalyst, hydrochloric acid and/or 14-hydroxycodeinone may be water-wet when used. In this regard, the quantity of water which may be added to the reaction in this way is not detrimental to the process provided the ratio of alcohol solvent:water is sufficiently large such that the oxycodone hydrochloride substantially precipitates out of the reaction mixture.

The hydrogenation catalyst may be a heterogeneous platinum group metal (PGM) catalyst. The catalyst should be selected such that the catalyst preferentially reduces the double bond between C-7 and C-8 rather than reducing the C═O bond at C-6 (see FIG. 1). In one embodiment, the heterogeneous catalyst is a heterogeneous platinum group metal (PGM) catalyst, for example, a heterogeneous palladium or platinum catalyst. In one embodiment, the heterogeneous platinum group metal (PGM) catalyst is a heterogeneous palladium catalyst. Examples of palladium catalysts include but are not limited to colloidal palladium, palladium sponge, palladium plate or palladium wire. Examples of platinum catalysts include but are not limited to colloidal platinum, platinum sponge, platinum plate or platinum wire.

The heterogeneous PGM metal catalyst may be a PGM on a solid support. The support may be selected from the group consisting of carbon, alumina, calcium carbonate, barium carbonate, barium sulfate, titania, silica, zirconia, ceria and a combination thereof. When the support is alumina, the alumina may be in the form of alpha-$Al_2O_3$, beta-$Al_2O_3$, gamma-$Al_2O_3$, delta-$Al_2O_3$, theta-$Al_2O_3$ or a combination thereof. When the support is carbon, the carbon may be in the form of activated carbon (e.g. neutral, basic or acidic activated carbon), carbon black or graphite (e.g. natural or synthetic graphite). An example of a heterogeneous PGM catalyst is palladium on carbon.

The catalyst loading may be up to about 20 mole %. In one embodiment, the catalyst loading may be up to 10 mole % and, in another embodiment, may be in the range of about 0.1-10.0 mole %.

While it is typically sufficient for a single charge of hydrogenation catalyst to be added to the reaction mixture, a second or further charge may be added and the hydrogenation continued if it has been determined (e.g. via in-process analysis) that the reaction has not gone to completion and starting material remains.

Conventionally, the hydrogenation of 14-hydroxycodeinone is carried out at an ambient temperature. By "ambient temperature", we mean a temperature of 30° C. or less. In the present process, however, the hydrogenation is carried out at one or more temperatures greater than ambient temperature i.e. greater than 30° C. and below the boiling point of the reaction mixture. The boiling point of the reaction mixture may vary depending on the pressure under which the hydrogenation reaction is conducted. In one embodiment, the hydrogenation may be carried out at one or more temperatures in the range of ≥ about 30° C. to about ≤ about 85° C. In one preferred embodiment, the hydrogenation is carried out at one or more temperatures in the range of ≥ about 30° C. to about ≤50° C., such as about 40° C.

There is no particular limitation on the pressure at which the hydrogenation is carried out. In this regard, the hydrogenation may conveniently be carried out with an initial hydrogen pressure in the range between about 30-55 psi, e.g. about 40±5 psi.

As mentioned above, the hydrogenation is carried out at one or more temperatures greater than ambient temperature i.e. greater than 30° C. and below the boiling point of the reaction mixture. The skilled person would understand and take into account the pressure of the reaction and the effect that it may have on the boiling point of the reaction mixture.

In carrying out the process of the invention at a temperature greater than ambient temperature, in which 14-hydroxycodeinone in an alcoholic solvent and hydrochloric acid is heated to temperature before it is exposed to the hydrogen gas, it is possible to obtain oxycodone hydrochloride with an improved impurity profile. In one embodiment, it is possible to significantly reduce the levels of 6α-oxycodol, an impurity which must be controlled to particular levels specified in Official Monographs such as the US Pharmacopeia. For example, the USP 33 Reissue for Oxycodone Hydrochloride specifies that the acceptance criterion for 6α-oxycodol cannot be more than 0.25%. However, the oxycodone hydrochloride ultimately prepared in a production campaign may have undergone several (or, indeed, many) processing treatments in order to reduce the level of 6α-oxycodol, as well as other impurities, to sufficiently acceptable low levels in order to conform to the required standard. The processing treatments therefore can typically result in extended processing times on plant and loss in product yield.

In carrying out the process of the present invention, however, the formation of 6α-oxycodol can be minimised in the reaction which produces it as an impurity, thus reducing the requirement for further processing.

Without wishing to be bound by theory, 6-oxycodol does not appear to be generated from oxycodone (see FIG. 1). Instead, it appears to be produced from 14-hydroxycodeinone which is reduced to 14-hydroxycodeine and it is this latter compound which results in the formation of 6-oxycodol. The hydrogenation process of the present invention therefore appears to influence the 14-hydroxycodeinone-14-hydroxycodeine-6-oxycodol pathway such that the quantity of 6α-oxycodol formed is at a reduced level. Accordingly, the hydrogenation process of the present invention may immediately meet the acceptance criterion specified for 6α-oxycodol in a single step thus improving the overall synthetic route of the oxycodone hydrochloride by increasing the yield of the desired product of the hydrogenation reaction (by decreasing the quantity of 14-hydroxycodeinone lost to impurity formation), as well as reducing or eliminating the requirement for later processing treatments.

The present invention provides a process wherein the oxycodone hydrochloride comprises 6α-oxycodol in an amount ≤ about 0.300 area % as determined by HPLC in the post-hydrogenation reaction mixture. In some embodiments, the oxycodone hydrochloride comprises 6α-oxycodol in an amount ≤ about 0.100 area % as determined by HPLC.

The pH of the initial reaction mixture may be in the range of about ≥2.5 to about ≤4.5. In some embodiments, the pH may be ≥ about 2.6. In some embodiments, the pH may be ≥ about 2.7. In some embodiments, the pH may be ≥ about 2.8. In some embodiments, the pH may be ≥ about 2.9. In some embodiments, the pH may be ≤ about 4.4. In some embodiments, the pH may be ≤ about 4.3. In some embodiments, the pH may be ≤ about 4.2. In some embodiments, the pH may be ≤ about 4.1. In one embodiment, the pH of the initial reaction mixture may be in the range of about ≥3.0 to about ≤ about 4.0, such as about 3.5. It has been observed that within this pH range the level of 6α-oxycodol may be less than 0.100 area % as determined by HPLC.

By a process carried out in one pot, we mean a process where successive processes are carried out in a single reactor, namely (a) the reduction of 14-hydroxycodeinone to oxycodone, (b) the formation of oxycodone hydrochloride, (c) the precipitation of oxycodone hydrochloride out of solution.

Other impurities which are also specified in the Official Monographs include α,β-unsaturated ketones (ABUKs), such as 14-hydroxycodeinone and codeinone. There has been much recent concern over ABUKs due to their proposed biological activities as genotoxins. As such, there is a continuing need to develop processes which produce low ABUK oxycodone alkaloid and low ABUK oxycodone salts, such as low ABUK oxycodone hydrochloride. Without wishing to be bound by theory, it appears that the 14-hydroxycodeinone which may be present as an impurity in oxycodone hydrochloride originates from two sources—firstly, residual unreacted 14-hydroxycodeinone starting material and secondly, indirectly from 8,14-dihydroxy-7,8-dihydrocodeinone which, it has been argued, converts to 14-hydroxycodeinone under acidic conditions. Thus, even if the reactions conditions are capable of driving a reaction to form oxycodone having <10 ppm of 14-hydroxycodeinone, the ABUK, 14-hydroxycodeinone, may be generated during salt formation via the dehydration of 8,14-dihydroxy-7,8-dihydrocodeinone. In this regard, 8,14-dihydroxy-7,8-dihydrocodeinone may be present in the hydrogenation of 14-hydroxycodeinone to oxycodone as it may be present as an impurity in the 14-hydroxycodeinone starting material. It may, therefore, be carried forward in the transformation of 14-hydroxycodeinone to oxycodone, as well as subsequent salt formation to form an oxycodone hydrochloride. Likewise, the ABUK codeinone may be generated during salt formation via the dehydration of the precursor 8-hydroxy-7,8-dihydrocodeinone.

In one embodiment, therefore, the oxycodone hydrochloride prepared according to the present invention comprises ≤ about 50 ppm of an α,β-unsaturated ketone, such as ≤ about 25 ppm of an α,β-unsaturated ketone, for example, ≤ about 15 ppm of an α,β-unsaturated ketone. In one preferred embodiment, the oxycodone hydrochloride comprises ≤ about 10 ppm of an α,β-unsaturated ketone. In another embodiment, the oxycodone hydrochloride is substantially free of an α,β-unsaturated ketone. The α,β-unsaturated ketone may be selected from the group consisting of 14-hydroxycodeinone, codeinone and a mixture thereof. Without wishing to be bound by theory, it is believed that the temperature at which the present invention is carried out (i.e. greater than ambient temperature) is capable of simultaneously dehydrating 8,14-dihydroxy-7,8-dihydrocodeinone (to produce 14-hydroxycodeinone), hydrogenating 14-hydroxycodeinone (to form oxycodone), dehydrating 8-hydroxy-7,8-dihydrocodeinone, if present (to form codeinone) and hydrogenating codeinone, if present (to form hydrocodone).

Before the reaction mixture is heated to temperature, the reaction vessel may be purged with one or more nitrogen/vacuum cycles (e.g. one, two, three or four cycles). During purging the reaction mixture may be agitated to encourage removal of dissolved oxygen. After the final purge cycle the vessel may be left under nitrogen and agitated (by either stirring or shaking) whilst the vessel is heated. Once the reaction mixture reaches the desired temperature, the hydrogenation reaction may begin by exposing the reaction mixture to hydrogen gas.

Alternatively, the reaction mixture may be heated to the desired temperature and held at that temperature before exposing the reaction mixture to the hydrogen gas. In one embodiment, therefore, the reaction mixture may be held at one or more temperatures above ambient for up to about 1 minute or more before the hydrogen gas is added. In another embodiment, the reaction mixture may be held at one or more temperatures above ambient for up to about 15 minutes or more before the hydrogen gas is added. In yet another embodiment, the reaction mixture may be held at one or more temperatures above ambient for up to about 6 hours or more before the hydrogen gas is added.

The hydrogenation reaction is carried out for a period of time until it is determined that the reaction is complete. Completion of the reaction may be determined by in-process analysis or by identifying that there is no longer an uptake of hydrogen gas. The reaction mixture may be held at temperature and pressure for up to about 24 hours.

On completion of the reaction, the reaction vessel may be cooled to ambient temperature and purged to remove excess hydrogen gas (or vice versa). The hydrogenation catalyst may be removed by any appropriate method, such as filtration (eg. over Celite™), and the filtrate (containing the oxycodone hydrochloride) may be further treated as desired.

The invention will now be described by way of the following non-limiting Examples and Drawings.

EXAMPLES

Analytical Method 1.1 Reagents and Materials:

| Reagent/Material | Supplier |
|---|---|
| Acetic Acid (HOAC) | J. T. Baker, HPLC Grade |
| Acetonitrile (ACN), HPLC Grade | Fisher, Optima, HPLC Grade |
| Sodium Hydroxide (NaOH), 1.0N | VWR Scientific Products |
| 1-Decanesulfanate, Sodium salt | HPLC Grade |
| PTFE HPLC Mobile Phase Filters | E.M. Science |
| Hydrochloric Acid (HCl) | Fisher Scientific |
| Methanol | Fisher, Optima, HPLC Grade |
| Codeine Phosphate | JM Reference Standard |
| 6α-Oxycodol | JM Reference Standard |
| Oxycodone Hydrochloride | JM Reference Standard |
| Oxycodone-N-oxide | JM Reference Standard |
| Thebaine | JM Reference Standard |
| 14-Hydroxycodeinone RS | JM Reference Standard |
| Triethylamine (TEA) HPLC Grade | Fisher, HPLC Grade |
| pH 1.68 Buffer | Alfa Aesar, SpecPure |
| pH 4.00 Buffer | Alfa Aesar, SpecPure |
| Column | Phenomenex Luna, $C_{18}(2)$, 3 μm, 100 × 4.6 mm OOD-4251-EO |

1.2 Instrumentation:

| Instrument | Description |
| --- | --- |
| Detector | Waters, 2487 UV/VIS Detector |
| Chromatograph | Waters, 2690 Separations Module |
| Data System | Chromatography Data System, current JM version |
| Balance | Mettler-Toledo, Model AT261, DeltaRange |
| pH Meter | Beckman, Model 320 |
| Purified Water | Milli-Q, A-10 Gradient System |

1.3 Operating Conditions:

| Conditions | Description | | | |
| --- | --- | --- | --- | --- |
| Injection Volume | 10 µl | | | |
| Temperature | 35° C | | | |
| Detection | UV at 280 nm | | | |
| Flow Rate | 1.5 mL/min | | | |
| | Time (min) | % MP A | % MP B | Curve |
| Linear Gradient (Mixing) Conditions | initial | 100 | 0 | 6 |
| | 20 | 90 | 10 | 6 |
| | 40 | 0 | 100 | 6 |
| | 45 | 0 | 100 | 6 |
| | 46 | 100 | 0 | 6 |
| | 55 | 100 | 0 | 6 |

1.4 Diluent Preparation:
Using concentrated HCl and Purified water, prepare a 0.1 N hydrochloric acid solution.
1.5 Mobile Phase Preparation:
Mobile Phase (MP) A:
  Weigh 2.22 g of Decane Sulfonic Acid, Sodium Salt and transfer into a suitable 1 L flask.
  Transfer 750 mL purified water, 100 mL MeOH and 150 mL ACN into the flask.
  Mix well to completely dissolve the ion-pairing salt.
  Add 20.0 mL of HOAc and 1.0 mL of TEA.
  Mixwell and adjust the apparent pH to 3.5 with HOAc (or NaOH, ~1 N).
  Filter and degas the solution.
Mobile Phase (MP) B:
  Weigh 2.22 g of Decane Sulfonic Acid, Sodium Salt and transfer into a suitable 1 L flask.
  Transfer 450 mL purified water, 400 mL MeOH, and 150 mL ACN into the flask.
  Mix well to completely dissolve the ion-pairing salt.
  Add 20.0 mL of HOAc and 1.0 mL of TEA.
  Mixwell and adjust the apparent pH to 3.5 with HOAc (or NaOH, 1 N).
  Filter and degas the solution.
1.6 Retention Times of Specified Analytes:

| Analyte | RT (min) | RRT |
| --- | --- | --- |
| Oxycodone-N-oxide | 5.0 | 0.26 |
| 6α-Oxycodol | 11.4 | 0.60 |
| Codeine | 14.4 | 0.75 |
| Oxycodone | 19.1 | 1.00 |
| 14-Hydroxycodeinone | 23.0 | 1.20 |
| Thebaine | 33.5 | 1.75 |

1.7 Sample Solution Preparation:
In duplicate, accurately weigh approximately 100 mg of the drug substance into a suitable 25 mL volumetric flask.
Pipette 5.0 mL of methanol into the flask.
Mix and sonicate until the sample is dissolved, limit sonication to 1 minute, allow to come to room temperature, then dilute to volume with diluent, and mix well.
1.8 RTM Preparation:
Stock Impurity RTM Solution
  Accurately weigh approximately 20 mg of each appropriate qualified reference impurity standard into a suitable 100 mL volumetric flask.
  Pipette 10.0 mL of methanol into the flask.
  Mix and sonicate until all solids are dissolved, limit sonication to 1 minute, then dilute to volume with diluent, and mix well.
0.5% Impurity RTM Solution
Transfer 5.0 mL of the stock impurity solution into a suitable 50 mL volumetric flask.
Dilute to volume with diluent. Mix well.
1.9 Resolution Solution Preparation:
Accurately weigh approximately 100 mg of Oxycodone HCl (test sample may be used) into a suitable 25 mL volumetric flask.
Dilute to volume with the 0.5% impurity standard solution.
1.10 System Equilibration:
After purging mobile phase through both reservoirs, pump Mobile Phase B for at least 20 minutes.
Switch to Initial assay conditions and pump for at least 20 minutes.
1.11 Procedure:
Separately inject in duplicate: the diluent as a blank and Resolution Solution.
Inject the 0.5% RTM solution.
Ensure that all system suitability requirements are met.
Perform duplicate injections of each sample preparation.
Perform a diluent injection at the end of the run.
Unspecified impurities detected should be identified by relative retention time (RRT) to Oxycodone.
1.12 Calculations:
Area % Specified Impurity (corrected for RRf):

$$\frac{(PA^{Imp})100}{(\text{Total }PA)(RRF)}$$

where: PA=peak area
  Imp=impurity
  RRf=Relative Response Factor

| RRf Factors (Report 2114): | |
| --- | --- |
| Impurity | RRF |
| Codeine | 1.163 |
| 6α-Oxycodol | 1.596 |
| Oxycodone-N-oxide | 0.927 |
| Thebaine | 6.017 |
| 14-Hydroxycodeinone | 1.238 |

$$\% \text{ Unspecified Impurities} = \frac{PA \text{ Unspecified } Imp}{\text{Total } PA \text{ in chromatogram}} \times 100\%$$

Figure 2:
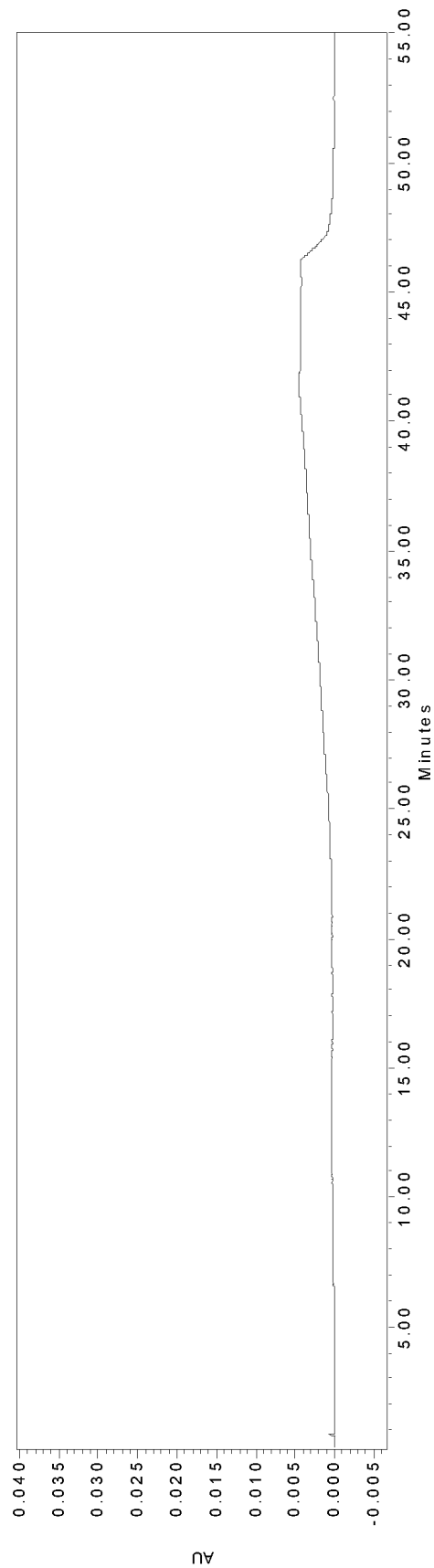
FIG. 2 shows a typical chromatogram using 0.1 N HCl/water acid solution as blank.

1.14 Typical Chromatograms
FIG. 2 shows a typical chromatogram using 0.1N HCl/water acid solution as blank.

Figure 3:
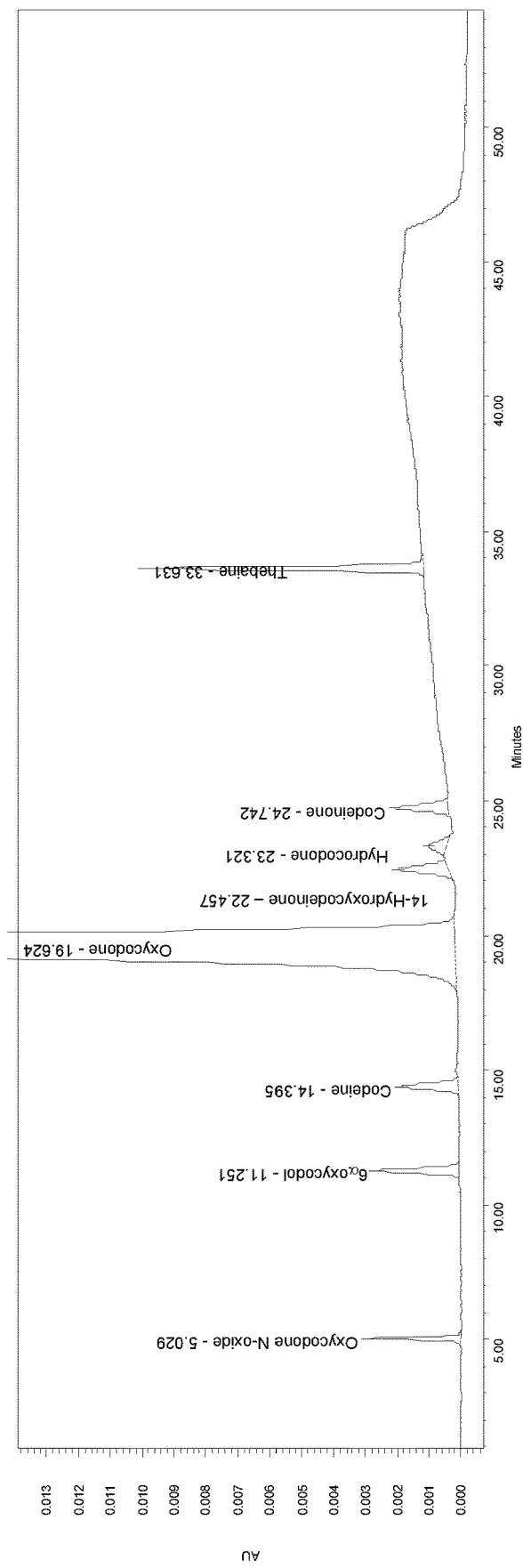
FIG. 3 shows a typical chromatogram of the retention time markers (RTM).

FIG. 3 shows a typical chromatogram of the retention time markers (RTM).

Figure 4:
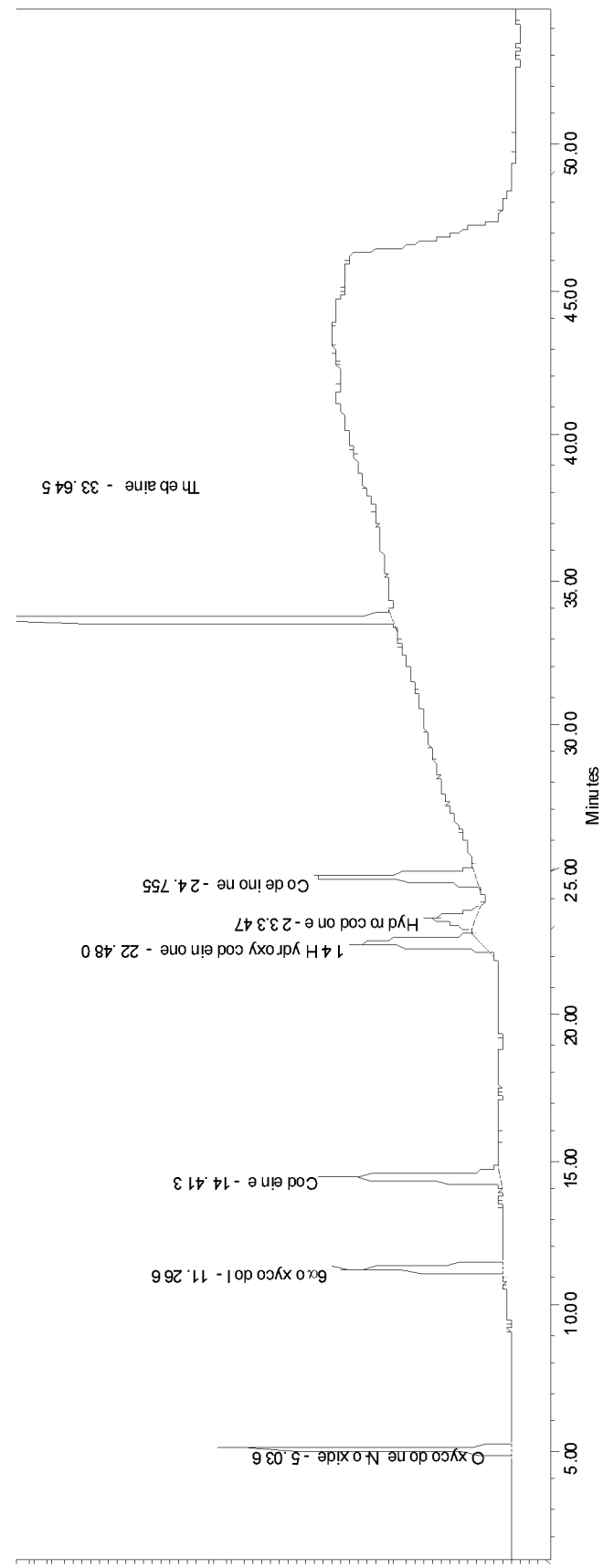
FIG. 4 shows a typical chromatogram of a 0.5% Impurity Standard solution.

FIG. 4 shows a typical chromatogram of a 0.5% Impurity Standard solution

Example 1: Experiment 1 (Table 1)

Charge to pressure vessel, jacket at 65° C.

30 g 14-hydroxycodeinone (FHC), 20 g water, 57 g ethanol (SDA-3A), 8.0 g 37% hydrochloric acid (pH 1.5), 0.3 g 5% Palladium on carbon catalyst (50% wet).

Purge reactor with nitrogen, batch temperature to not less than 60° C.

Cycle hydrogen to 20 psi four times to establish hydrogen atmosphere.

Pressurize vessel with hydrogen to 20 psi (pounds per square inch).

Agitation to 600 rpm, reset jacket to 80° C.

After 24 hours, vent hydrogen, purge with nitrogen. Filter (hot) through Celite™ to remove catalyst.

Rinse vessel and filter cake with ethanol (~50 mL). Cool batch to <5° C. over two hours. Isolate solid by filtration, wash with chilled ethanol.

The subsequent experiments are carried out in a similar manner, at the temperature, pressure, pH and using the catalyst indicated in Table 1.

Example 2: Analytical Results for Experiments 1-6

TABLE 1

| Experiment | Time hours | Temp ° C. | HCl eq./pH | $H_2$ psi | Catalyst 5%, 1.0 wt % | Impurities (%) Oxycodol | Impurities (%) unspec | Impurities (%) total |
|---|---|---|---|---|---|---|---|---|
| Temperature and Pressure variation |||||||||
| 1* | 23 | 80 | 1.0/pH 1.5 | ~20 | Pd/C | 0.74 | 1.72 | 2.48 |
| 2* | 23.5 | 30 | 1.0/pH 1.5 | 40-45 | Pd/C | 0.56 | 0.65 | 1.26 |
| 3* | 26 | 20 | 1.0/pH 1.0 | 40-45 | Pd/C | 0.61 | 0.65 | 1.33 |
| Catalyst variation |||||||||
| 4* | 25 | 40 | 1.0/pH 2.0 | 40-45 | Pd/BaSO₄ | 0.58 | 0.52 | 1.10 |
| 5 | 24 | 40 | 1.0/pH 4.1 | 40-45 | Pd/Alumina | 0.24 | 1.14 | 1.39 |
| 6* | 24.5 | 40 | 1.0/pH 1.0 | 40-45 | Pd/BaCO₃ | 0.57 | 0.56 | 1.18 |

*Not according to the invention

From Table 1 some reaction conditions were identified as preferred: hydrogen pressure of 40-45 psi, 5% Palladium on carbon catalyst at 1% loading as wet, and reaction temperature of 40° C. (Experiment 5). The next series of experiments is intended to demonstrate reproducibility as well as define the acceptable pH range (Table 2).

Example 3: Experiment 9 (Table 2)

Charge to pressure vessel, jacket at 40° C. 25 g FHC, 20 g water, 57 g ethanol (SDA-3A), 37% hydrochloric acid to pH 3.0, 0.25 g 5% Palladium on carbon catalyst (50% wet).

Purge reactor with nitrogen, batch temperature to ~40° C.

Cycle hydrogen to 45 psi three times to establish hydrogen atmosphere.

Pressurize vessel with hydrogen to 45 psi (pounds per square inch).

Agitation to 600 rpm.

After 24 hours, vent hydrogen, purge with nitrogen. Heat batch to ~60° C. to dissolve product and filter (hot) through Celite™ to remove catalyst. Rinse vessel and cake with ethanol (~50 mL). Cool batch to <5° C. over two hours. Isolate solid by filtration, wash with chilled ethanol. Dry solid under vacuum at ~55° C., 16.8 g.

Example 4: Experiment 10 (Table 2)

Charge to pressure vessel, jacket at 40° C.

25 g FHC, 20 g water, 57 g ethanol (SDA-3A), 37% hydrochloric acid to pH 4.0, 0.25 g 5% Palladium on carbon catalyst (50% wet).

Purge reactor with nitrogen, batch temperature to ~40° C.

Cycle hydrogen to 45 psi three times to establish hydrogen atmosphere.

Pressurize vessel with hydrogen to 45 psi (pounds per square inch).

Agitation to 600 rpm.

After 24 hours, vent hydrogen, purge with nitrogen. Heat batch to ~60° C. to dissolve product and filter (hot) through Celite™ to remove catalyst. Rinse vessel and cake with ethanol (~50 mL). Cool batch to <5° C. over two hours. Isolate solid by filtration, wash with chilled ethanol. Dry solid under vacuum at ~55° C., 17.4 g.

Example 5: Analytical Results for Experiments 7-11

TABLE 2

| Experiment | Reaction Conditions (24 h) | | | | Impurities (%) | | |
|---|---|---|---|---|---|---|---|
| | pH | T ° C. | $H_2$ psi | catalyst | Oxycodol | Unspec. | Total |
| 7* | 1.1 | 40 | 40-45 | 5% Pd/C | 0.35% | 0.45% | 0.80% |
| 8* | 2.0 | 40 | 40-45 | 5% Pd/C | 1.01% | 0.44% | 1.45% |
| 9 | 3.0 | 40 | 40-45 | 5% Pd/C | 0.07% | 0.50% | 0.57% |
| 10 | 4.0 | 40 | 40-45 | 5% Pd/C | 0.10% | 0.49% | 0.59% |
| 11* | 5.0 | 40 | 40-45 | 5% Pd/C | 0.30% | 0.42% | 0.72% |

*Not according to the invention

The invention claimed is:

1. A process for preparing oxycodone hydrochloride, said process comprising hydrogenating 14-hydroxycodeinone in an alcoholic solvent and hydrochloric acid to form oxycodone hydrochloride, wherein
    (a) the hydrogenation is carried out in the presence of a heterogeneous platinum group metal (PGM) hydrogenation catalyst and hydrogen gas,
    (b) the hydrogenation is carried out at one or more temperatures greater than ambient temperature, wherein the 14-hydroxycodeinone in an alcoholic solvent and hydrochloric acid is heated to temperature before it is exposed to the hydrogen gas,
    (c) the pH of the 14-hydroxycodeinone in an alcoholic solvent and hydrochloric acid is in the range of about ≥2.5 to about ≤4.5,
    (d) the process is carried out in one pot; and
    (e) the oxycodone hydrochloride comprises 6α-oxycodol in an amount <0.300 area % as determined by HPLC.

2. The process according to claim 1, wherein the oxycodone hydrochloride substantially precipitates out of solution when the process for preparing oxycodone hydrochloride is carried out in the range of ≥about 30° C. to about ≤about 45° C.

3. The process according to claim 1, wherein the oxycodone hydrochloride is substantially dissolved when the process is carried out in the range of ≥about 45° C. to about ≤about 85° C.

4. The process according to claim 1, wherein the alcoholic solvent is selected from the group consisting of methanol, ethanol, n-propanol, and isopropanol or mixtures thereof.

5. The process according to claim 4, wherein the alcoholic solvent is ethanol.

6. The process according to claim 1, wherein the hydrogen gas pressure is between about 30-55 psi.

7. The process according to claim 6, wherein the hydrogen gas pressure is about 40 psi±5 psi.

8. The process according to claim 1, wherein the one or more temperatures greater than ambient temperature are in the range of ≥about 30° C. to about ≤about 85° C.

9. The process according to claim 8, wherein the one or more temperatures greater than ambient temperature are in the range of ≥about 30° C. to about ≤50° C.

10. The process according to claim 9, wherein the one or more temperatures greater than ambient temperature is about 40° C.

11. The process according to claim 1, wherein the pH is in the range of about ≥3.0 to about ≤4.0.

12. The process according to claim 1, wherein the heterogeneous platinum group metal hydrogenation catalyst is Pd/C.

13. The process according to claim 1, wherein the oxycodone hydrochloride comprises 6α-oxycodol in an amount ≤about 0.100 area % as determined by HPLC.

14. The process according to claim 1, wherein the oxycodone hydrochloride comprises ≤about 25 ppm of an α,β-unsaturated ketone.

15. The process according to claim 14, wherein the oxycodone hydrochloride comprises ≤about 10 ppm of an α,β-unsaturated ketone.

* * * * *